United States Patent
Shirley et al.

(10) Patent No.: US 12,168,098 B2
(45) Date of Patent: Dec. 17, 2024

(54) HEAT MOISTURE EXCHANGER (HME) HAVING ROTATABLE BYPASS CHANNEL FOR USE IN A MEDICAL VENTILATION SYSTEM

(71) Applicant: Ventlab, LLC, Grand Rapids, MI (US)

(72) Inventors: Mark Nicholas Shirley, Kalamazoo, MI (US); Mark Zyzelewski, Kalamazoo, MI (US)

(73) Assignee: Ventlab, LLC, Grand Rapids, MI (US)

( * ) Notice: Subject to any disclaimer, the term of this patent is extended or adjusted under 35 U.S.C. 154(b) by 1007 days.

(21) Appl. No.: 17/023,299

(22) Filed: Sep. 16, 2020

(65) Prior Publication Data
US 2020/0405994 A1 Dec. 31, 2020

Related U.S. Application Data

(63) Continuation-in-part of application No. 15/214,129, filed on Jul. 19, 2016, now abandoned.

(51) Int. Cl.
| | | |
|---|---|---|
| A61M 16/10 | (2006.01) | |
| A61M 16/06 | (2006.01) | |
| A61M 16/08 | (2006.01) | |

(52) U.S. Cl.
CPC ........ *A61M 16/1045* (2013.01); *A61M 16/06* (2013.01); *A61M 16/0816* (2013.01); *A61M 2205/583* (2013.01)

(58) Field of Classification Search
CPC .............. A61M 16/1045; A61M 16/06; A61M 16/0816; A61M 2205/583
See application file for complete search history.

(56) References Cited

U.S. PATENT DOCUMENTS

| | | | |
|---|---|---|---|
| 5,460,172 A * | 10/1995 | Eckerbom | A61M 16/085 128/205.12 |
| 5,992,413 A | 11/1999 | Martin, Jr. et al. | |
| 6,415,788 B1 | 7/2002 | Clawson et al. | |
| 6,550,476 B1 * | 4/2003 | Ryder | A61M 16/1045 128/205.12 |
| 6,588,421 B1 * | 7/2003 | Diehl | A61M 16/12 165/130 |
| 6,792,946 B1 * | 9/2004 | Waldo, Jr. | A62B 9/003 128/205.12 |
| 6,976,488 B2 | 12/2005 | Halerin | |
| 7,069,928 B1 * | 7/2006 | Waldo, Jr. | A61M 16/1045 128/911 |
| 7,594,509 B2 | 9/2009 | Burk | |
| 7,624,731 B2 | 12/2009 | Walstrom | |
| 7,634,998 B1 | 12/2009 | Fenley | |
| 7,921,846 B1 | 4/2011 | Marler et al. | |

(Continued)

*Primary Examiner* — Tu A Vo
(74) *Attorney, Agent, or Firm* — Sheridan Ross P.C.

(57) ABSTRACT

A heat moisture exchanger (HME) having a rotatable bypass channel includes a rotating cylinder having a first port and an outer cylinder having a second port attached to the rotating cylinder. A half-cylinder shaped foam insert is configured within the rotating cylinder to heat and moisturize air moving through the HME. The cylinder is configured to create a rotational bypass to air using an angled diverter moving between the first port and second port such that the rotating cylinder can be moved between a position for engaging the foam insert and a bypass position for bypassing the foam insert.

13 Claims, 13 Drawing Sheets

(56) References Cited

U.S. PATENT DOCUMENTS

| | | | |
|---|---|---|---|
| 2004/0084046 A1* | 5/2004 | Halperin | A61M 16/1045 128/201.13 |
| 2004/0123974 A1* | 7/2004 | Marler | A61M 16/1055 165/9.4 |
| 2005/0121074 A1* | 6/2005 | Pittaway | A61M 16/0808 137/171 |
| 2006/0157056 A1* | 7/2006 | Burk | A61M 16/1045 128/201.13 |
| 2006/0219243 A1* | 10/2006 | Walstrom | A61M 16/1045 128/201.28 |
| 2009/0095296 A1 | 4/2009 | Wruck et al. | |
| 2009/0301474 A1* | 12/2009 | Korneff | A61M 16/1045 128/201.13 |
| 2010/0282247 A1* | 11/2010 | Kadrichu | A61M 15/0086 128/200.14 |
| 2013/0068219 A1* | 3/2013 | Collazo | A61M 16/20 128/201.13 |
| 2017/0224946 A1* | 8/2017 | Mühlbauer | A61M 16/201 |

* cited by examiner

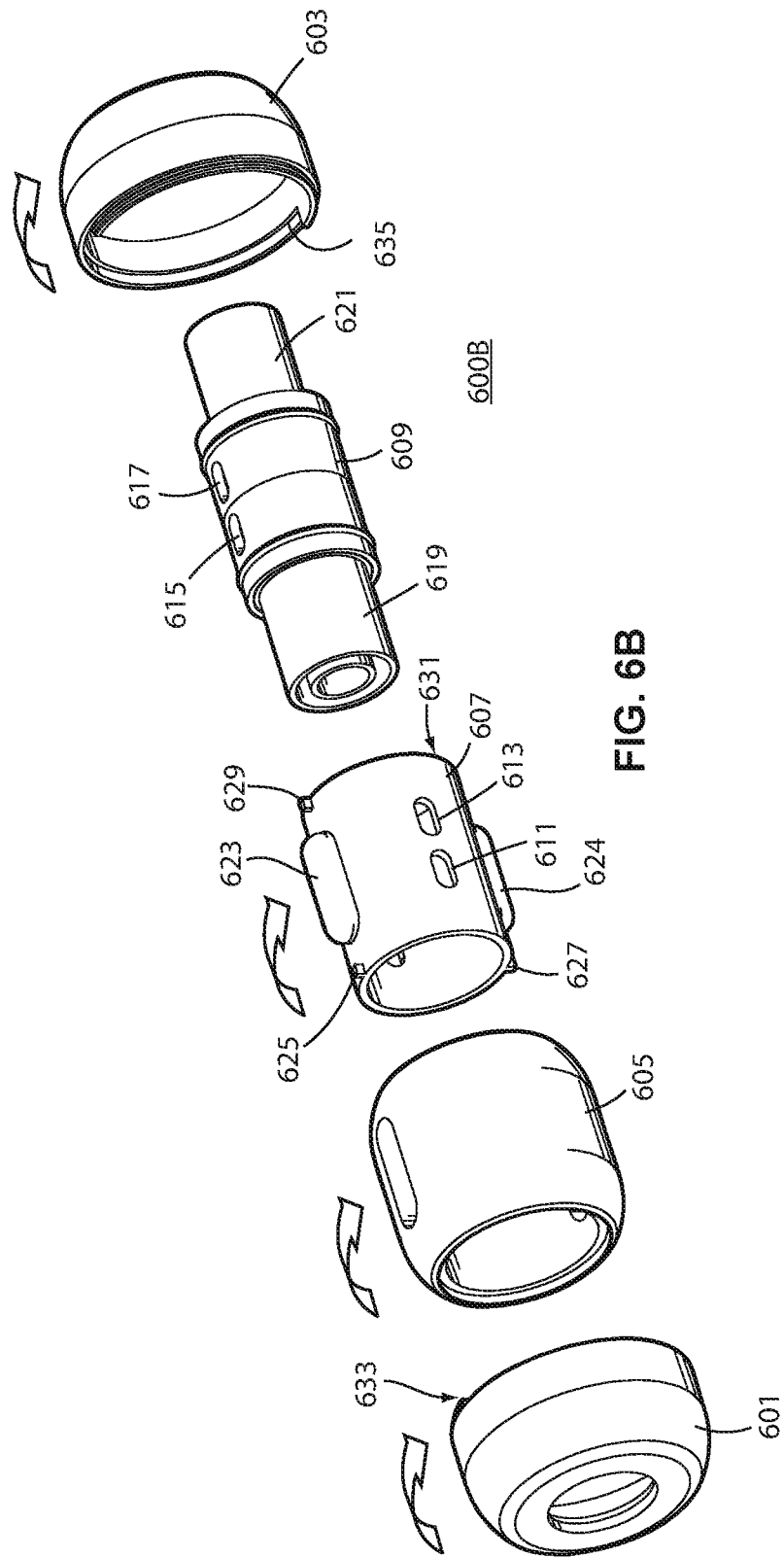

HEAT MOISTURE EXCHANGER (HME) HAVING ROTATABLE BYPASS CHANNEL FOR USE IN A MEDICAL VENTILATION SYSTEM

CROSS-REFERENCE TO RELATED APPLICATIONS

This application is a continuation-in-part of U.S. patent application Ser. No. 15/214,129 filed Jul. 19, 2016, the disclosure of which is incorporated herein by reference in its entirety.

FIELD OF THE INVENTION

The present invention relates generally to heat and moisture exchanger (HME) and more particularly an HME having a rotatable bypass channel.

BACKGROUND

HMEs are devices used with medical applications for mechanically ventilated patients. The HME is used to help prevent complications due to drying of the respiratory mucosa, such as mucus plugging and endotracheal tube (ETT) occlusion. HMEs are one type of commercial humidification system, which also include non-heated-wire humidifiers and heated-wire humidifiers. Humidification and suctioning are often necessary to manage secretions in patients on mechanical ventilation. Thus, the HME works as an addition to ventilator circuit that uses a passive heat and moisture exchanger and a heated component to filter, heat, and humidify the gases supplied to the ventilated patient.

In the lungs a temperature of 37° C. and 100% relative humidity (RH) is the ideal condition for the ciliary activity. If the conditions are too warm or cold, the cilia beat slower and at some point not at all. During normal nasal inspiration, air of 22° C. and 40% RH is conditioned into air of 32° C. and 99% RH at the level of the trachea. The effect of the increased resistance (compared to stoma breathing without HME) in laryngectomy patients is poorly understood, but HMEs add a variable resistance to the airflow resistance, depending on the flow rate, though the outcomes of studies are not consistent.

HME cassettes with an electrostatic filter are typically designed to enhance the protection against airborne microbes and to help to reduce the transfer of viruses and bacteria. Wearing an HME cassette does not compensate for the loss of upper airway filtration of smaller particles such as bacteria and viruses since the pores of the HME foam are larger than the diameter of the infectious particles. Only larger particles are filtered by the HME however for all intents and purposes, the HME does not filter any particles, it only heats and humidifies. The basic components of the HME are foam, paper, or a substance which acts as a condensation and absorption surface. The foam material is often impregnated with hygroscopic salts such as calcium chloride, to enhance its water-retaining capacity.

When using an HME, it is often necessary to introduce aerosolized medication to the patient. As it is necessary to prevent the drugs from contaminating the sponge-like filter, it is necessary to introduce a bypass around the filter in order to prevent contamination. Present solutions to the bypass are often hard to use or actuate.

SUMMARY OF THE INVENTION

A heat moisture exchanger (HME) unit for use with medical ventilation equipment includes a rotating cylinder and outer cylinder such that the rotating cylinder can be rotated to control air moving through the HME so that it is either heated/humidified or bypassed. In another embodiment, the HME includes a rotatable bypass channel where a rotating cylinder includes a first port and an outer cylinder has a second port attached to the rotating cylinder. A foam insert is configured within the rotating cylinder where the rotating cylinder and outer cylinder are configured to create a rotational bypass to air moving between the first port and second port such that the rotating cylinder can be moved between a position for engaging the foam insert. Air moves through the foam insert substantially orthogonally around a longitudinal center of the rotating cylinder when in an HME mode, where the HME also includes a bypass position for bypassing the foam insert allowing air to move substantially orthogonally around the longitudinal center of the rotating cylinder without engaging the foam insert when in the bypass position.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 6B is an exploded view showing rotation of components for bypassing the filter.

Figure 1A:
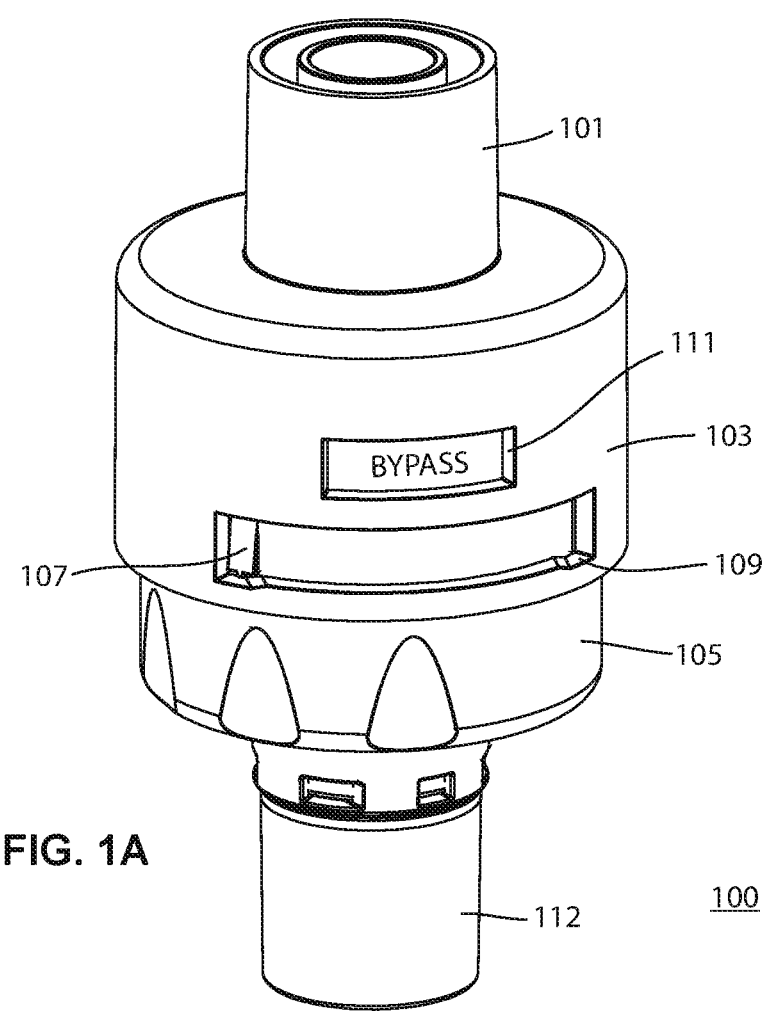
FIG. 1A is perspective view of embodiment of the invention illustrating the HME in a bypass mode.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a heat and moisture exchanger. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1A is perspective view of an HME that uses a rotatable housing. The HME 100 includes a first or "patient" port 101 that connects with and may be integral with the outer cylinder 103. The outer cylinder 103 is configured to operate with a rotating cylinder 105. The rotating cylinder works with a key 107 and keyway to limit movement of the rotating cylinder 105. The key 107 projects from a surface of the rotating cylinder housing 105 into the keyway 109. The keyway 109 is a rectangular slot configured within the outer cylinder 103. When aligned, the key 107 limits the rotational motion of the rotating cylinder 105 such that the key 107 will act as a stop on both sides of the keyway 109. The configuration of the HME includes either an HME or "engaged" mode; or a bypass mode. The engaged mode engages at least one foam insert requiring the air to pass through it while the bypass mode, bypass the air around the foam insert. As used herein, the terms "air" and "airstream" are used generically meaning breathing gases for the patient such as ambient air, medical oxygen, vapor type inhaled medications and various combinations thereof. The mode is displayed using a window 111 configured within the outer cylinder 103. Finally, the rotating cylinder 105 is connected to a second or output port 112. The output port 112 is also sometimes called a rotating mask port or machine port for allowing the patient's breathing or ventilation mask and tubing to be connected to the HME 100.

Figure 1B:
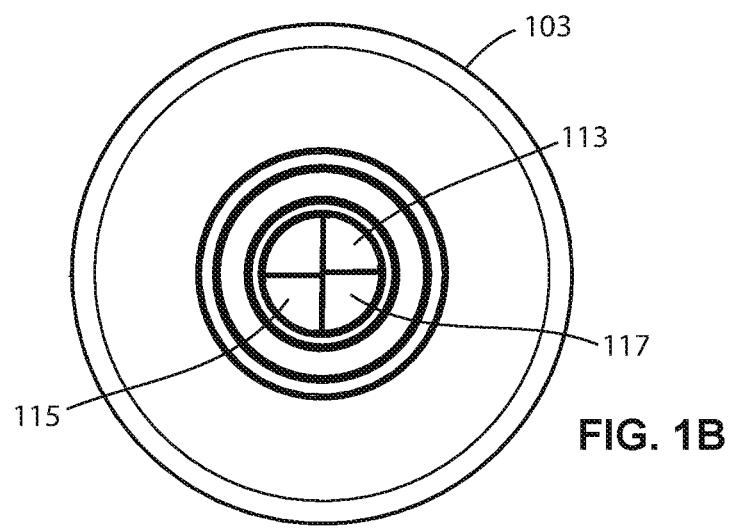
FIG. 1B is a top view of the HME shown in FIG. 1A.

FIG. 1B is a top view of the HME shown in FIG. 1A. Looking inside the input port 101, the foam inserts are oriented into a bypass position such that air moving though the HME will move though the bypass channels 113, 115. Section 117 is part of the cylinder 103, designed to occlude the HME channels when in the bypass mode, and vice-versa. The bypass orientation allows air to pass through the HME substantially unimpeded.

Figure 2A:
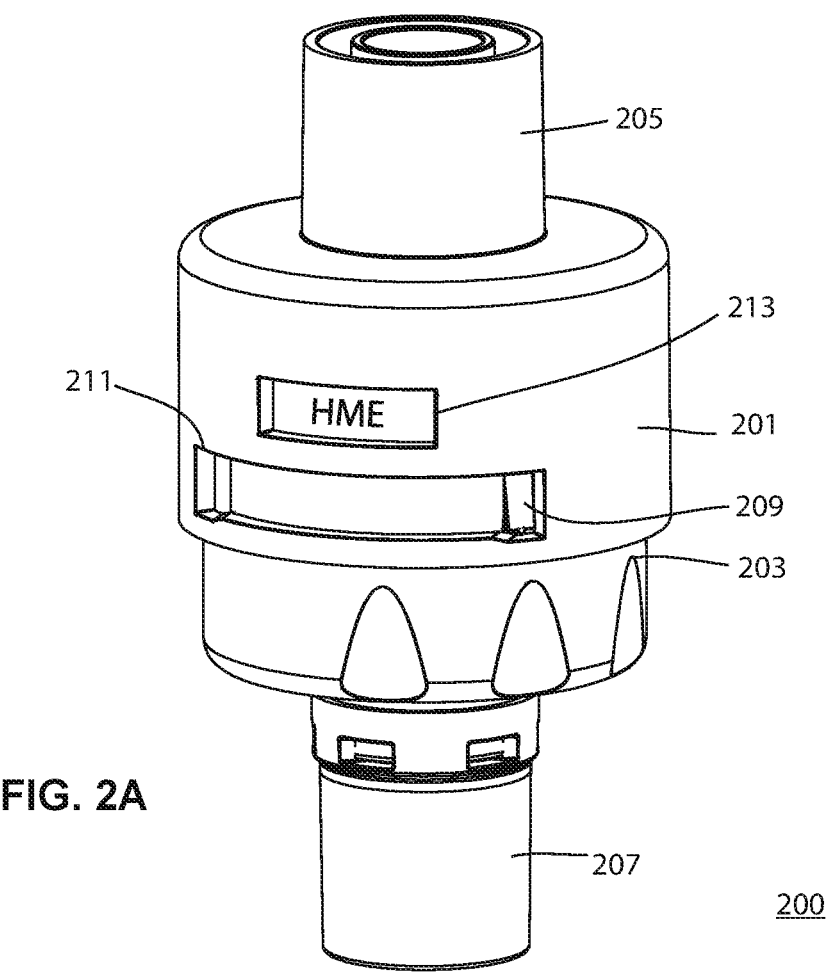
FIG. 2A is a perceptive view of the HME rotated so that it acts as a humidifier.

FIG. 2A is a perspective view of the HME rotated into its filtered or HME position. The outer cylinder 201 and rotating cylinder 203 are configured so that air moving though the HME from the inlet port 205 to the rotating mask port 207 moves through foam inserts that work to heat and humidify the air moving through them. The heat and humidity is provided by the patient's inhalation and exhalation breaths that work to warm and humidity one or more foam inserts within the HME. In this configuration, the stop 209 is positioned at the opposite side of the keyway 211 to that shown in FIG. 5A. The HME is configured into the HME mode when the outer cylinder 201 is rotated and/or configured such that HME label or placard is displayed in the window 213.

Figure 2B:
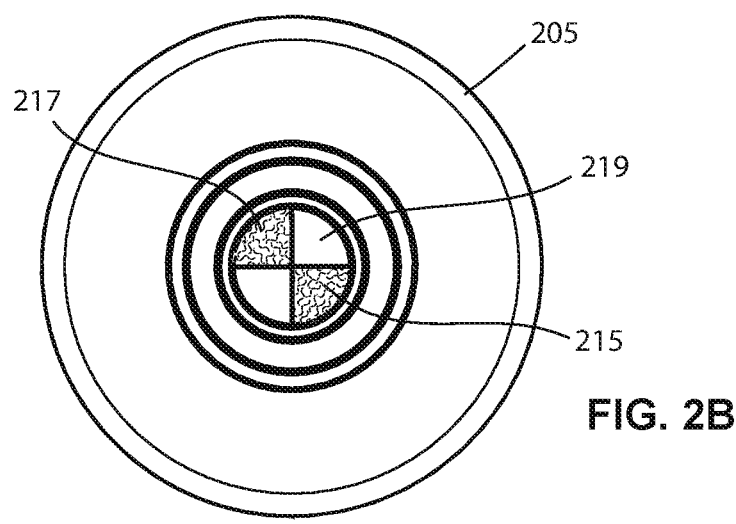
FIG. 2B is a top view of the HME shown in FIG. 2A.

FIG. 2B is a top view of the HME shown in FIG. 2A. Looking down into the inlet port 205, the foam chambers 215, 217 are oriented so that air will pass through them. Section 219 is part of the outer cylinder 201 and is designed to occlude the HME channels when in bypass mode, and vice-versa.

Figure 3:
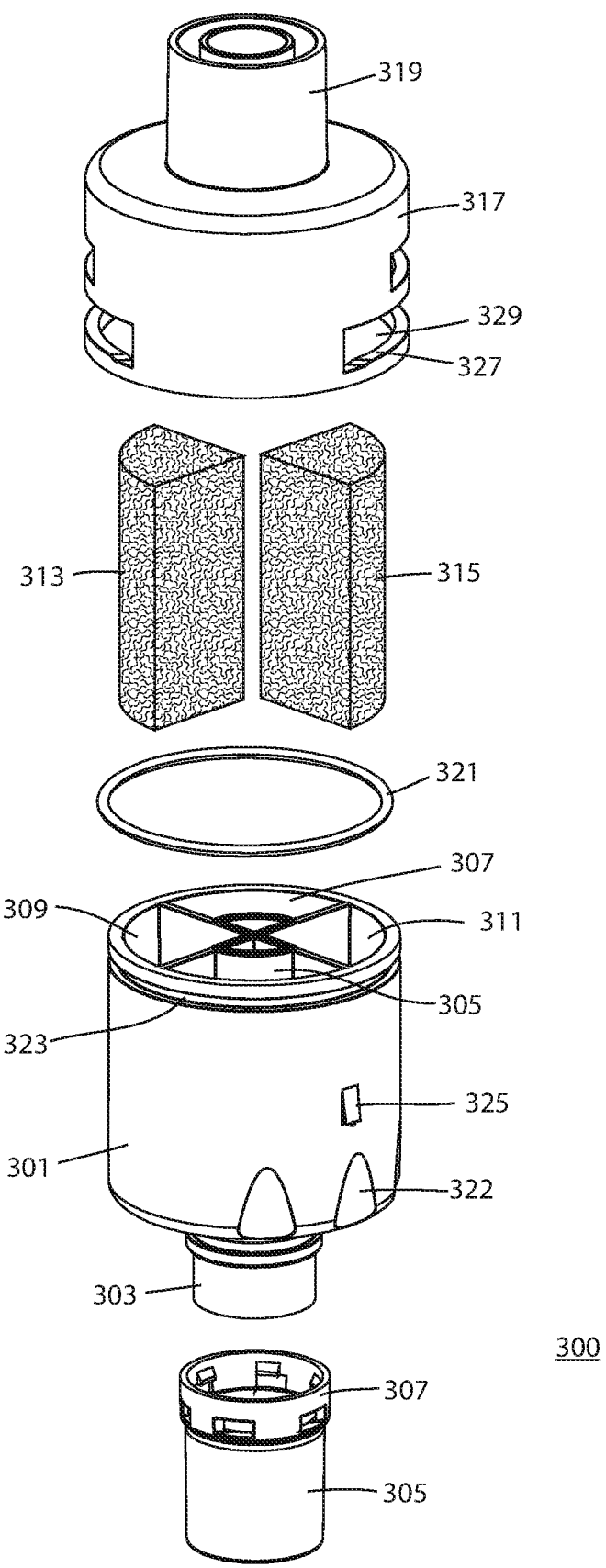
FIG. 3 is an exploded view of the HME shown in FIG. 1A and FIG. 2A.

FIG. 3 is an exploded view of the HME shown in FIG. 1A and FIG. 2A. The HME 300 includes a rotating cylinder 301 that includes a port 303 that is substantially cylindrical in shape and connects to a rotating mask port 305. The rotating mask port 305 has an attachment collar 307 for securing itself to a snap-on connection or alternatively a threaded guide on the outer surface of the port 305. The rotating mask port 305 rotates about the attachment collar 307 allowing it to move while connected to tubing or the like. The rotating cylinder 301 is substantially cylindrical in shape and includes a plurality of chambers for allowing air to either pass unimpeded though the cylinder or alternatively through one or more foam inserts that are configured therein. More specifically, a plurality of walls within rotating cylinder 301 form both a one or more bypass chambers 304, 306 and foam chambers 309, 311. The bypass chambers are configured within the cylinder to be 180 degrees opposed and similarly the bypass chambers are also configured to be 180 degrees opposed. When viewed from above, the walls forming the bypass chambers 304, 306 and foam chambers 309, 311 form a cross or X-like shape. In use, the foam inserts 313, 315 are inserted and frictionally engaged within foam chambers 309, 311 respectively for allowing the air passing though the inserts to be heated moisturized and/or humidified. This heating and moistening of the foam inserts 313, 315 occur from the patient's inhalation and exhalation breathing that works to subsequently warm the air moving through them. The foam inserts 313, 315 are substantially triangular having a wedge-like shape and are sized to frictionally engage longitudinally within the respective foam chamber 309, 311.

An outer cylinder is also cylindrically shaped and includes an input port 319 for porting air to and from the HME 300. The outer cylinder 317 is sized to partially fit over an end of the rotating cylinder 301 that is open and exposes the foam inserts 313, 315. An O-ring 321 is configured within a slot or groove 323 on the rotating cylinder 301 for providing a seal and preventing air from escaping between the rotating cylinder 301 and the outer cylinder 321. The rotating cylinder 301 further includes one or more finger dimples 322 for allowing the user to grip the rotating cylinder 301 during movement. When assembled, a snap or key 325 engages within a keyway 327 for limiting rotational movement of the rotating cylinder 301 to approximately 90 degrees. A window 329 is provided for displaying the operating positon of the HME e.g. HME mode or bypass mode.

Thus, an embodiment of the invention includes a heat exchange moisturizer (HME) having a rotatable bypass channel that includes a rotating cylinder having a first port and an outer cylinder having a second port attached to the rotating cylinder. One or more foam inserts are configured within the rotating cylinder to heat and provide humidity and moisture to the air moving though the HME using the patient inhalation and exhalation breaths. A key located on the surface of the rotating cylinder along with a keyway are configured within the outer cylinder so that the key and keyway limit rotational movement of the rotating cylinder such that the rotating cylinder can be moved between a position for engaging the at least one foam insert and a bypassed position for bypassing the at least one foam insert.

Figure 4A:
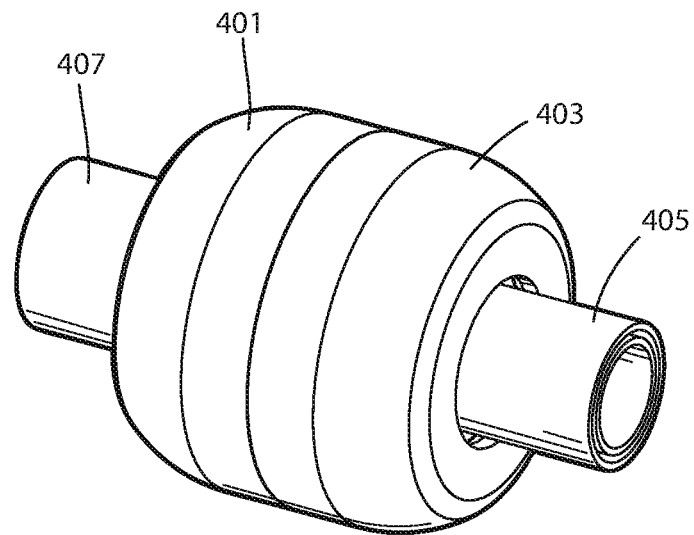
FIG. 4A is a perspective view of the HME in accordance with an alternative embodiment of the invention.
Figure 4B:
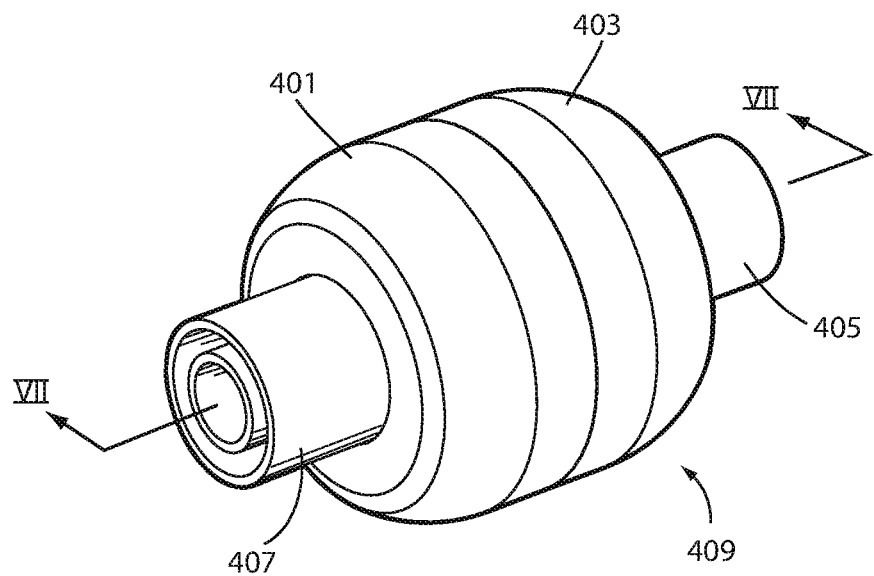
FIG. 4B is a perspective view of the HME illustrating the opposite side to that shown in FIG. 4A.

FIG. 4A is a perspective view of the HME in accordance with another embodiment of the invention. FIG. 4B is a perspective view of the HME illustrating the opposite end to that shown in FIG. 4A. With regard to both FIGS. 4A and 4B, the HME 400 includes a first half cover 401 and second half cover 403 that join to form a substantially small housing 404 for use with medial ventilation equipment. Each half of the housing 404 is generally frusto-conical shaped with truncated ends where the joining of the first half cover 401 and second half cover 403 occurs at the wide ends of each half cover. The half covers are frictionally engaged to one another using a key and keyway structure to form a unitary body welded together via ultrasonic welding. An entry port 405 is centrally positioned at one end and within the housing allowing air to enter the HME 400. Similarly, an exit port 407 is centrally positioned within, and at the opposite end, of the housing 404. The exit port 407 is used for allowing air to exit the HME. Those skilled in the art will recognize that the entry port 105 and exit port 407 are both sized according to ISO medical standards so that standardized ventilation tubing can be connected to both ends of the HME 400. As will be described herein, the first half cover 401 and second half cover 403 can rotate with respect to components within the HME 400 enabling it to be used in either an HME or a "bypass" mode.

Figure 5:
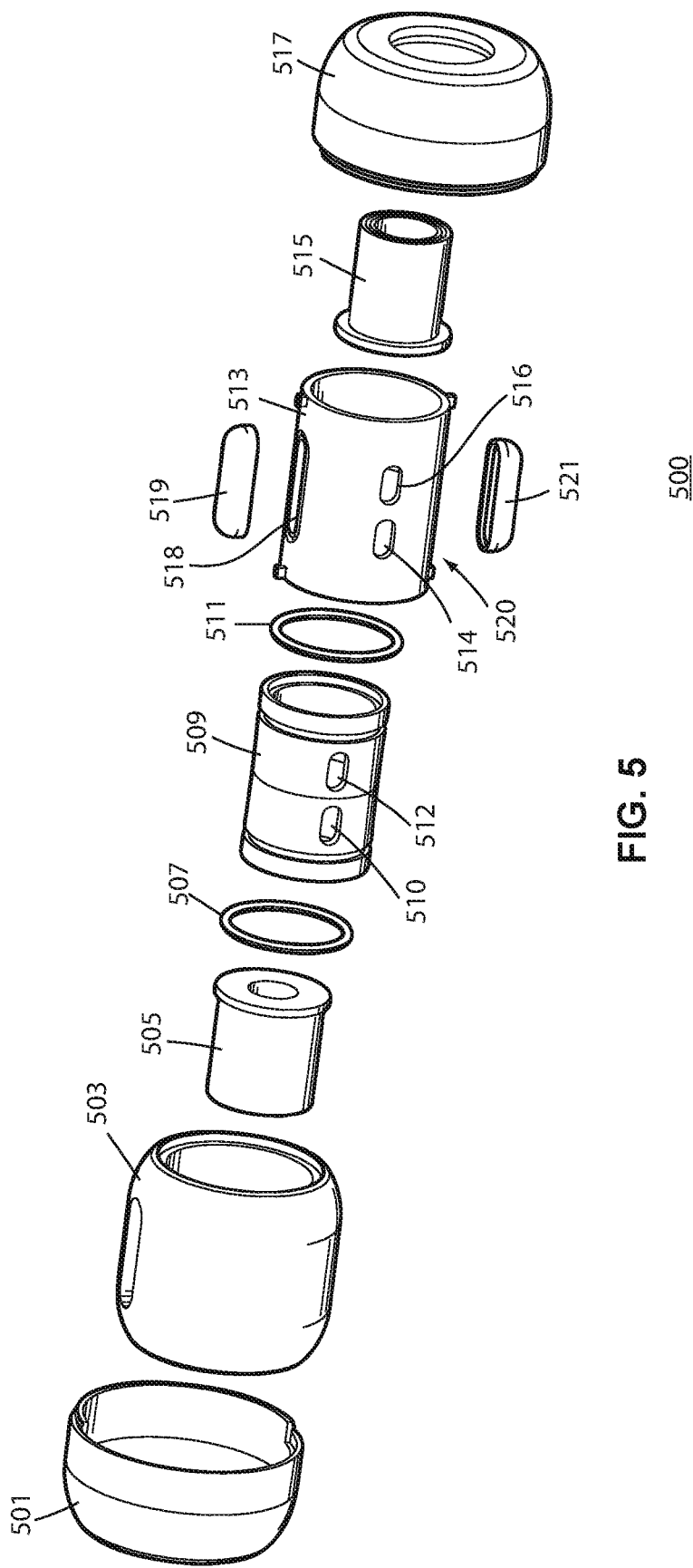
FIG. 5 is an exploded view showing components of the HME.

FIG. 5 is an exploded view showing various internal components of the HME. The HME 500 includes foam insert 503. The insert 503 is a sponge-like foam material used to collect both heat and moisture from the patient's exhaled breath. The foam insert 503 is a simple cylindrical shape with a die cut hole though its middle. The form inserts 503 acts solely to heat and humidity the air and does not truly act as a filter to particulate matter.

The HME 500 further includes an inner cylinder 509 whose outer diameter is smaller in size than that of the insert 503. The inner cylinder 509 includes two elongated holes 510, 512 along the body of its housing. When the insert 503 is positioned over the inner cylinder 509, ports 510 and 512 provide direct access by the patient airstream to the foam insert 503. At the ends of the inner cylinder 509 are respective input and output ports for allowing the airflow through the inner cylinder 509 when using ventilation equipment. More specifically, a female port 505 is used to connect HME to ventilation equipment. An O-ring 507 works to provide a seal with a corresponding grove located on the outer surface of cylinder 509. The port 505 is typically a female shape and is an entry port, sized to an ISO standard. Similarly, a male port 515 is also sized to an ISO standard and is positioned to abut the opposite side of the inner cylinder 509. An O-ring 511 is used with a corresponding groove on the outer surface of cylinder 509 for sealing and preventing air from escaping between components. The male port 515 is typically an exit port for air moving though the HME.

Further, a middle cylinder 513 is configured to be positioned over the inner cylinder 509 and is sized to be greater in diameter than the inner cylinder 509. The middle cylinder 513 includes two elongated holes 514, 516 substantially adjacent to one another on its body. The elongated holes 514, 516, can be aligned with holes 510, 512 and are used to channel air entering the entry port through the insert 503. The middle cylinder 513 also includes two elongated holes 518, 520 that are spaced 180 degrees apart circumferentially around the body of the middle cylinder 513. As described herein, the holes 518, 520 are used in connection with a respective bypass channel 519, 521. The bypass channel 519, 521 works to isolate the air from insert 503, providing a bypass and preventing it from entering the foam insert 503. Each bypass channel 519, 521 operates as a capsuled type cover or chamber for isolating each respective void 518, 5220 allowing the airstream to pass through it without contracting the insert 503.

In order to contain the HME 500, a first half cover 501 and a second half cover 517 work to form a housing. Both the first half cover 501 and second half cover 517 mechanically engage with one another to form a mirrored frusto-conically shaped housing holding all of the internal components of the HME in compression. In use, the first half cover 501 and second half cover 517 can be allowing the airstream to be routed either though the insert 503 or in a bypass mode around the insert 503.

Figure 6A:
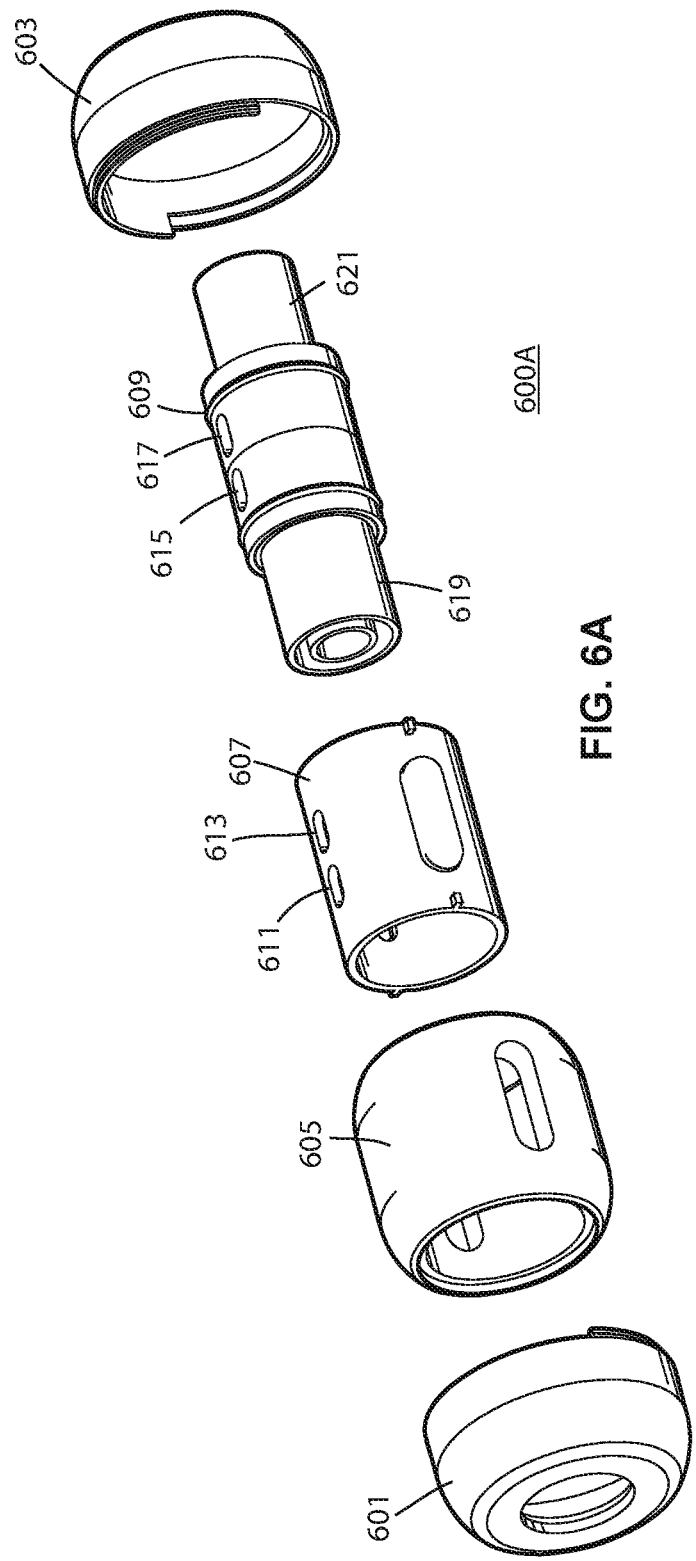
FIG. 6A is an exploded view illustrating rotating components of the HME.

FIG. 6A and FIG. 6B are exploded views illustrating the rotation of components within the HME for routing the incoming airflow though the foam insert or bypassing the foam insert. With regard to FIG. 6A illustrates an HME mode where the first outer cover 601 and second outer cover form a rotatable housing and work to hold the foam insert 605, middle cylinder 607 and inner cylinder 609 within the housing. The elongated holes 611, 613 on the middle cylinder 607 are shown in alignment with the elongated holes 615, 617 in the inner cylinder 609. Thus, air entering the input port will pass though elongated holes 611, 613 and elongated holes 615, 617 entering the foam insert 605 that is positioned on and directly over these holes before exiting the exit port 621.

With regard to FIG. 6B, this illustrates actuation of the bypass mode where the first outer cover 601, second outer cover 603 as well as the foam insert 605, middle cylinder 607 are rotated in relation to the inner cylinder 609. In the bypass mode, the elongated holes 611, 613 in the middle cylinder 607 are rotated 90 degrees to align with the elongated holes in the inner cylinder 609. In this embodiment, air entering the input port 619 is routed though the elongated holes 615, 617 in the bypass channels 623, 624, where the air will then directly exit the output port 621. When oriented in this manner, airflow will not pass through the foam insert 605. This allows vapor type medications or the like to be used in the ventilator airstream without the worry of contamination. The middle cylinder 607 also includes a plurality of alignment tabs 625, 6 27, 629, 631. The alignment tabs 625, 627, 629, 631 are sued for pre-weld alignment in the manufacturing of the HME.

Figure 7A:
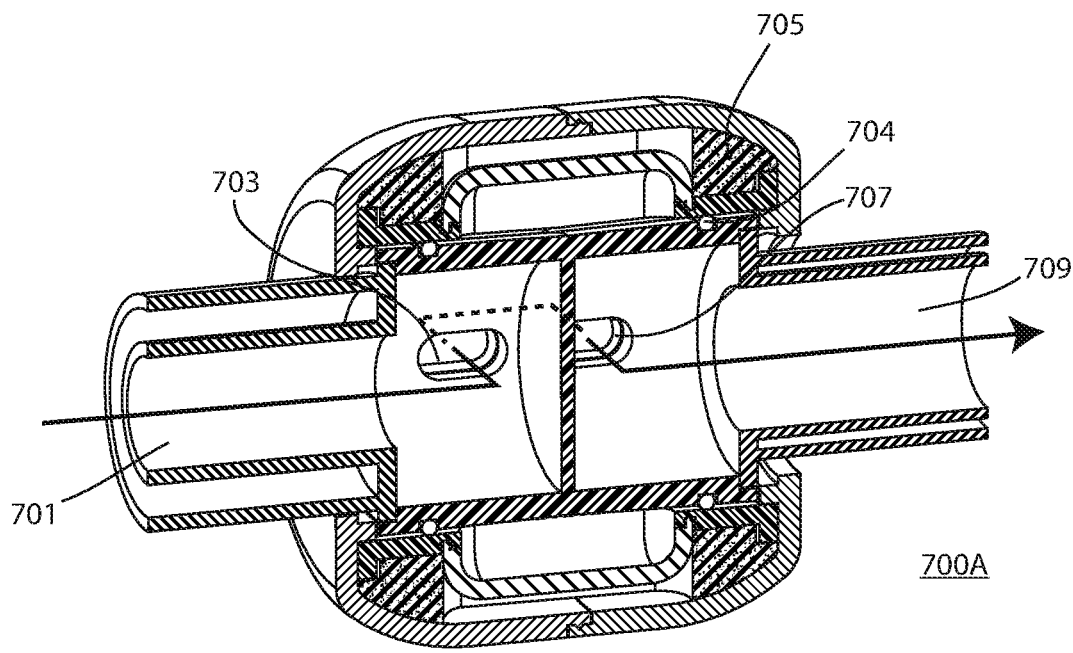
FIG. 7A is a cross-sectional view of the HME shown in FIG. 4B illustrating a closed bypass.
Figure 7B:
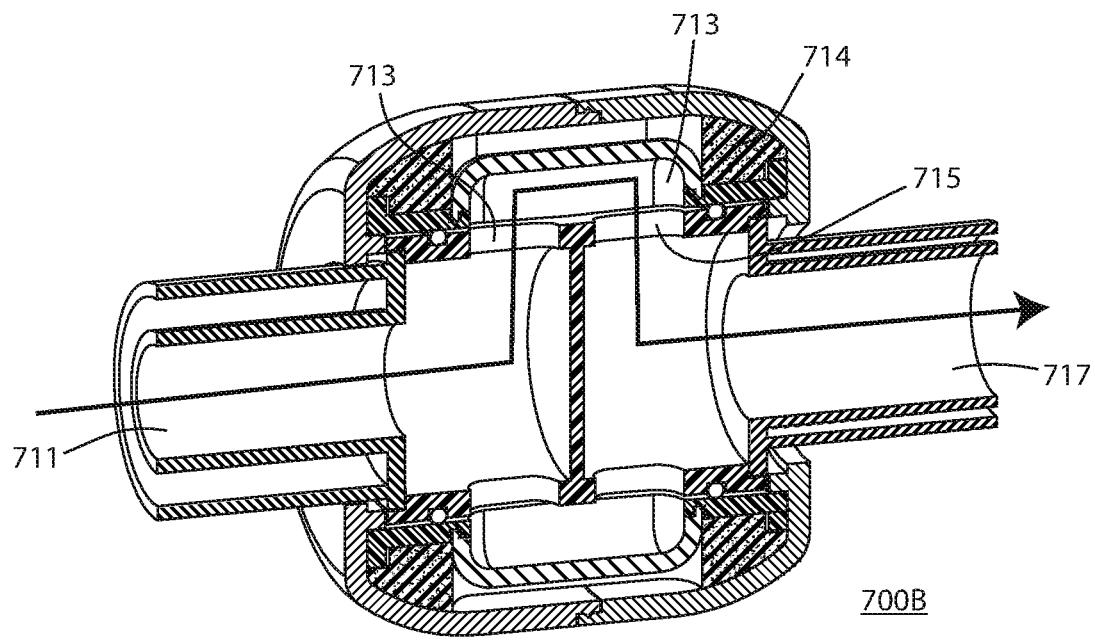
FIG. 7B is a cross-sectional view of the HME shown in FIG. 7A illustrating an open bypass.

FIG. 7A is a cross-sectional view of the HME shown through lines IV-IV in FIG. 7B illustrating use of the HME mode where air is passed though the foam insert. More specifically, the HME 700A operates by directing air at the input port 701 though the elongated hole 703 in the inner cylinder 704. The airstream then passes though the foam insert 705 where the air can be heated and humidified. It is then directed though the elongated hole 707 where the airstream is directed though the exit port 709.

FIG. 7B is a cross-sectional view of the HME shown through lines IV-IV in FIG. 4B illustrating the bypass mode where the components are rotated 90 degrees to that shown in FIG. 4A. In this configuration, HME 700B is shown where air enters the input port 711 and is directed though the elongated hole 713. This configuration directs the airstream though the bypass channel 713 where it is isolated from the foam insert 714. The air then moves though the elongated hole 715 where it exits though exit port 717. As seen with regard to FIG. 7A and FIG. 7B, the rotating cylinder and outer cylinder are configured to create a rotational bypass to air moving between the first port and second port such that the rotating cylinder can be moved between a position for engaging the at least one foam insert where air moves through the at least one foam insert moving substantially orthogonally around a longitudinal center of the rotating cylinder in an HME mode, and a bypass position for bypassing the at least one foam insert allowing air to move substantially orthogonally around the longitudinal center of the rotating cylinder without engaging the foam insert in a bypass mode.

Thus the heat exchange moisturizer (HME) includes an inner cylinder having an input port and output port; a middle cylinder surrounding the inner cylinder; a foam insert surrounding the middle cylinder for providing moisture and/or heat to air entering the input port before exiting the output port; and wherein the middle cylinder includes at least one bypass channel that is rotatably actuated for allowing air entering the input port to bypass the foam insert for directly exiting the output port. The one bypass channel is a comprised of an elongated chamber attached to the middle cylinder. The foam filter includes a cutout for accommodating the at least one bypass channel and the middle cylinder includes a filter port for allowing air to pass though the foam insert. The input port and output port include a head portion used in combination with a ring for sealing the input port and output port to the inner cylinder. The first half cover and second half cover the form a rotatable housing surrounding the foam insert and work to hold the foam filter, inner cylinder, and outer cylinder in compression.

Thus, an embodiment of the invention defines a heat exchange moisturizer (HME) having an inner cylinder, a middle cylinder surrounding the inner cylinder and a foam insert surrounding the middle cylinder. The foam insert provides heat and moisture to the airstream entering the input port before exiting the output port. A unique embodiment of the invention allows the middle cylinder to include at least one bypass channel that is rotatably actuated for allowing air entering the input port to bypass the foam insert and directly exiting the output port in the inner cylinder.

Figure 8A:
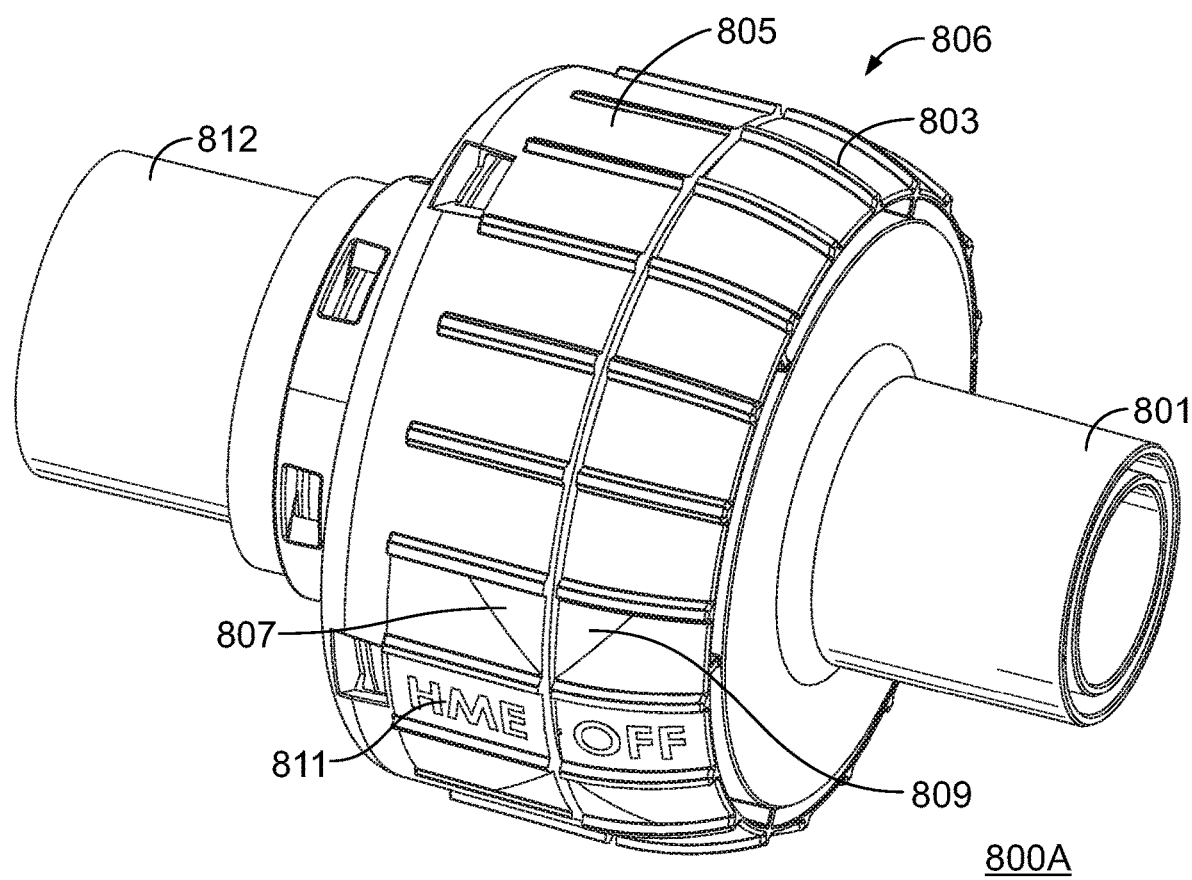
FIG. 8A is perspective view of an alternative embodiment of the invention illustrating the HME in an open bypass mode.
Figure 8B:
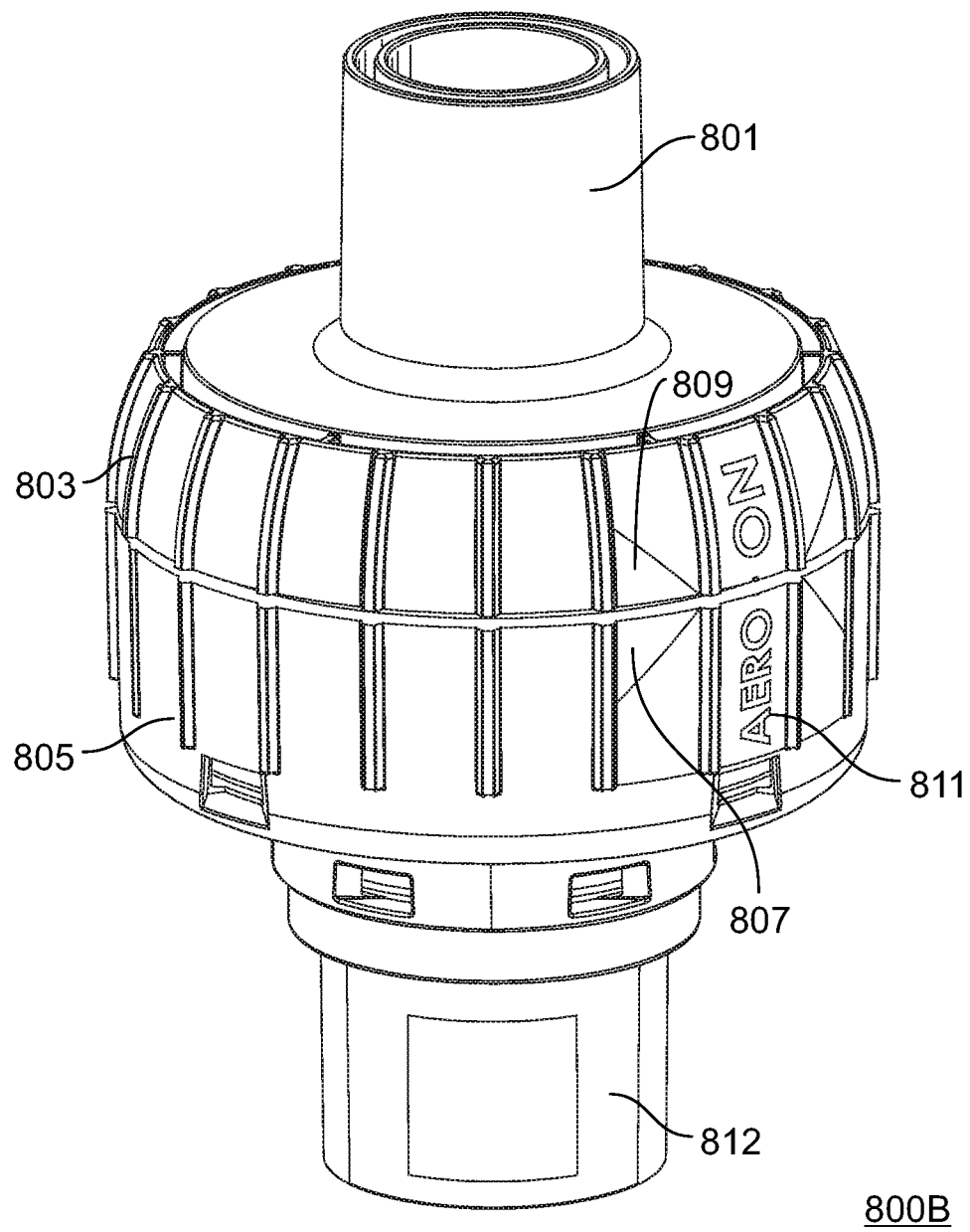
FIG. 8B is a perspective view of an alternative embodiment of the invention illustrating the HME in an closed bypass mode.

FIG. 8A and FIG. 8B are perspectives view of an HME that use a rotatable housing according to yet another embodiment of the invention. The HME 800A/800B include a first or "patient" port 801 that connects with and may be integral with the first housing 803. The first housing 803 is sized and configured to operate with a second housing 805 that joins to first housing 803 to form a rotating cylinder 806 that is in a substantially cylindrical configuration. Thus, the first housing 803 and second housing 805 rotate upon one another for enabling the control of airflow though the rotating cylinder 806. Orientation of the first housing 803 and second housing 805 work with arrows or other indicia located on each housing enabling the arrow to be aligned to indicate the HME is properly configured for use. As noted herein, the HME 800A/800B operates either in an "AERO ON" mode; or a "bypass" mode. The AERO ON mode engages at least one foam insert that works as a filter and/or cleaner requiring the air to pass through it while the bypass mode allows the air to be bypassed and/or routed around the filter. In FIG. 8A, the indicia 811, indicates an "HME OFF" or bypass mode of operation, and is displayed on the surface of the rotating cylinder 806. In FIG. 8B, the indicia 811 indicates an engaged or "AERO ON" mode. Finally, the rotating cylinder 806 is connected to a second or output port 812. As noted herein the output port 812 is also sometimes called a rotating mask port or machine port for allowing the patient's breathing or ventilation mask and tubing to be connected to the HME 800A/800B.

Figure 9:
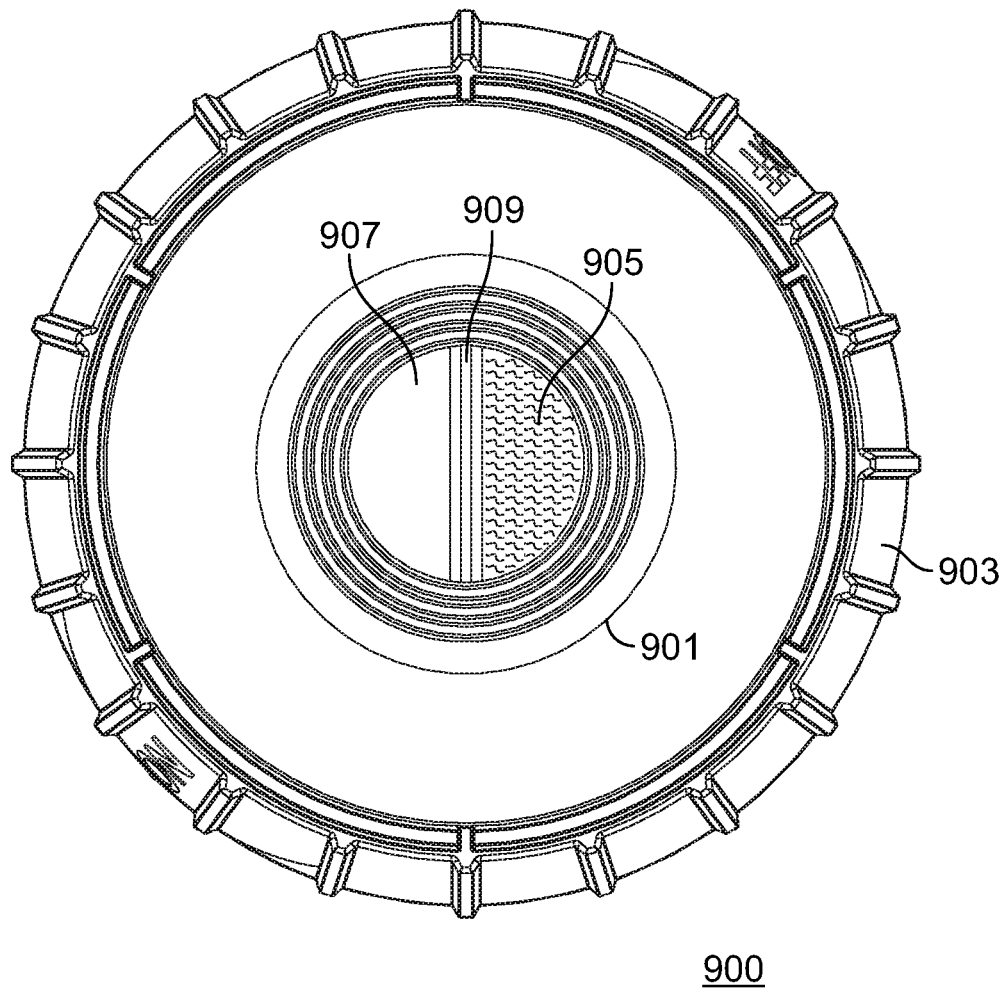
FIG. 9 is a top view of the HME shown in FIG. 8A.

FIG. 9 is a top view of the HME shown in FIG. 8A and FIG. 8B. Looking inside the input port 901, it is configured with the first housing 903, where a single foam insert 905 is oriented into a bypass position such that air moving though the HME will move into and through the bypass channel 907. When in the AERO ON mode, the foam insert holds moisture and is half-cylindrically shaped covering approximately one-half of the channel or airway making up the input port 901. The heat and humidity provided by the patient's inhalation and exhalation breath(s) work to warm and/or humidify the foam insert 905 within the first housing 903. A wall, such as section 909, is configured inside the input port 901 and works to divide and hold the foam insert 905 into position within the first housing. As noted herein, when the bypass orientation allows air to pass through the HME substantially unimpeded offering a substantially unrestricted airflow.

Figure 10:
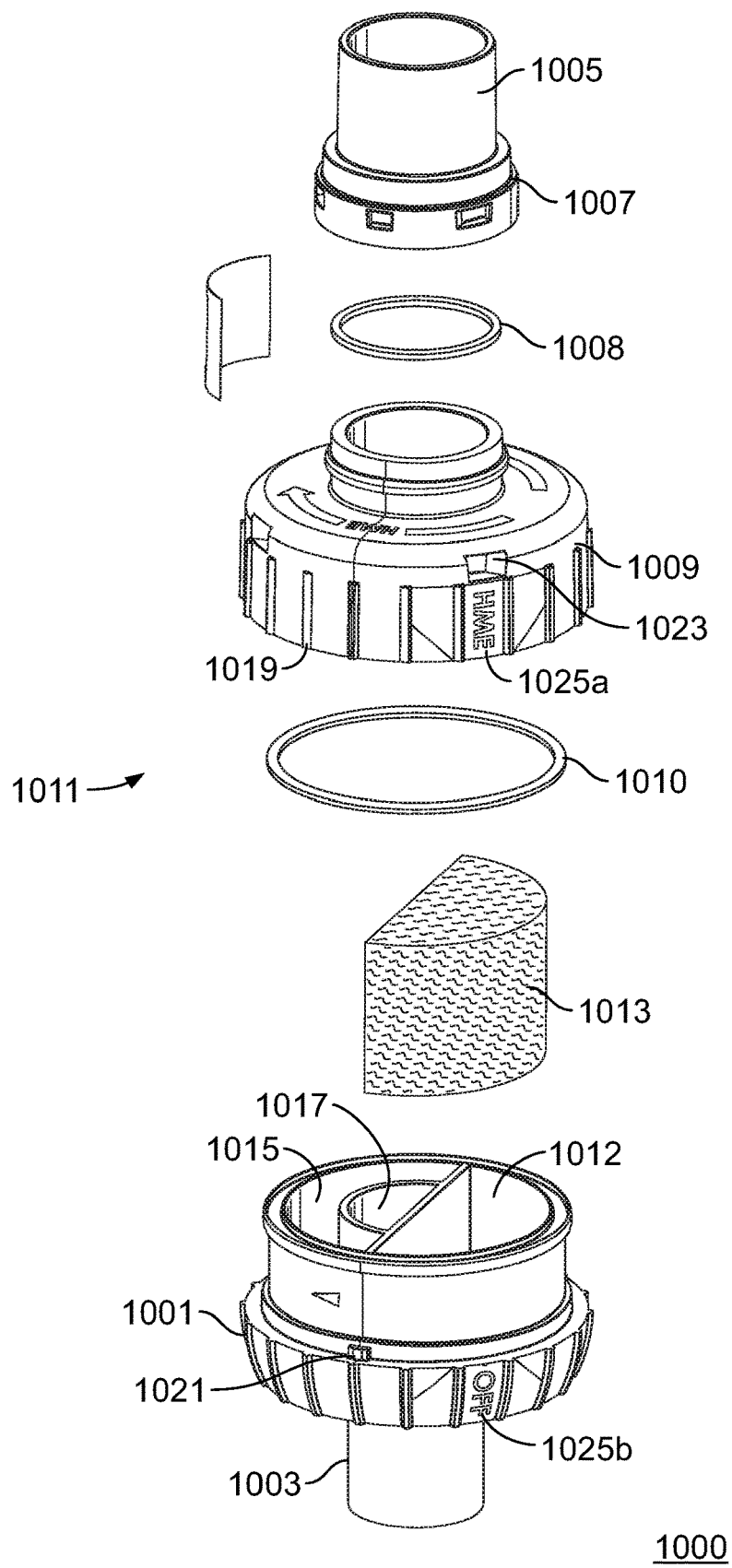
FIG. 10 is an exploded view showing components of the HME according to an alternative embodiment of the invention.

FIG. 10 is an exploded view of the HME shown in FIGS. 8A and 8B. The HME 1000 includes a first housing 1001 that includes a port 1003 that is substantially cylindrical in shape and communicates with a "swivel port" such as rotating mask port 1005. The rotating mask port 1005 has an attachment collar 1007 for securing itself to a snap-on connection with a second housing 1009 or alternatively a threaded guide on the outer surface of the port 1005. Instead of utilizing an overlap of parts, a first O-ring 1008 works as a gasket to improved seal or connection between the attachment collar 1007 and the second housing 1009. The O-ring 1008 provides an airtight seal between the attachment collar 1007 and second housing 1009. The rotating mask port 1005 rotates about the attachment collar 1007 allowing it to move while connected to tubing or the like. The first housing 1001 and second housing 1009 form a rotating cylinder 1011 where the first housing 1001 and second housing 1009 rotate independently. The rotating cylinder 1011 is substantially cylindrical in shape and includes a plurality of chambers 1012 for allowing air to either pass unimpeded though the cylinder or alternatively through a foam insert 1013 that is configured therein.

More specifically, a plurality of walls within first housing 1001 form bypass chambers 1015, 1017 and foam chamber 1012. The bypass chambers are configured within the first housing 1001 to be 180 degrees opposed from the foam chamber 1012. In use, the foam insert 1013 is inserted and frictionally engages within foam chamber 1012 for allowing the air passing though the insert to be heated, moisturized and/or humidified. As noted herein, the heating and moistening of the foam insert 1013 occurs from the patient's inhalation and exhalation breathing that works to subsequently warm the air moving through them. The foam insert 1013 has semi-circular half-cylinder shape and is sized to frictionally engage longitudinally within foam chamber 1012.

The first housing 1001 has a cylindrical-like outer shape and includes an input port 1003 for porting air to and from the HME 1000. The second housing 1009 is sized to partially fit over an end of the first housing 1001 and is sealed to prevent air from escaping using a second O-ring 1010. The rotating cylinder 1011 further includes one or more finger dimples 1019 for allowing the user to grip the rotating cylinder 1011 during movement. When assembled, a snap or key 1021 engages within a keyway side the second housing 1009 where a stop 1023 limits rotational movement of the rotating cylinder 1011 to approximately 90 degrees. Indicia 1025a/1025b are provided for displaying the operating position of the HME e.g. engaged "AERO ON".

Figure 11B:
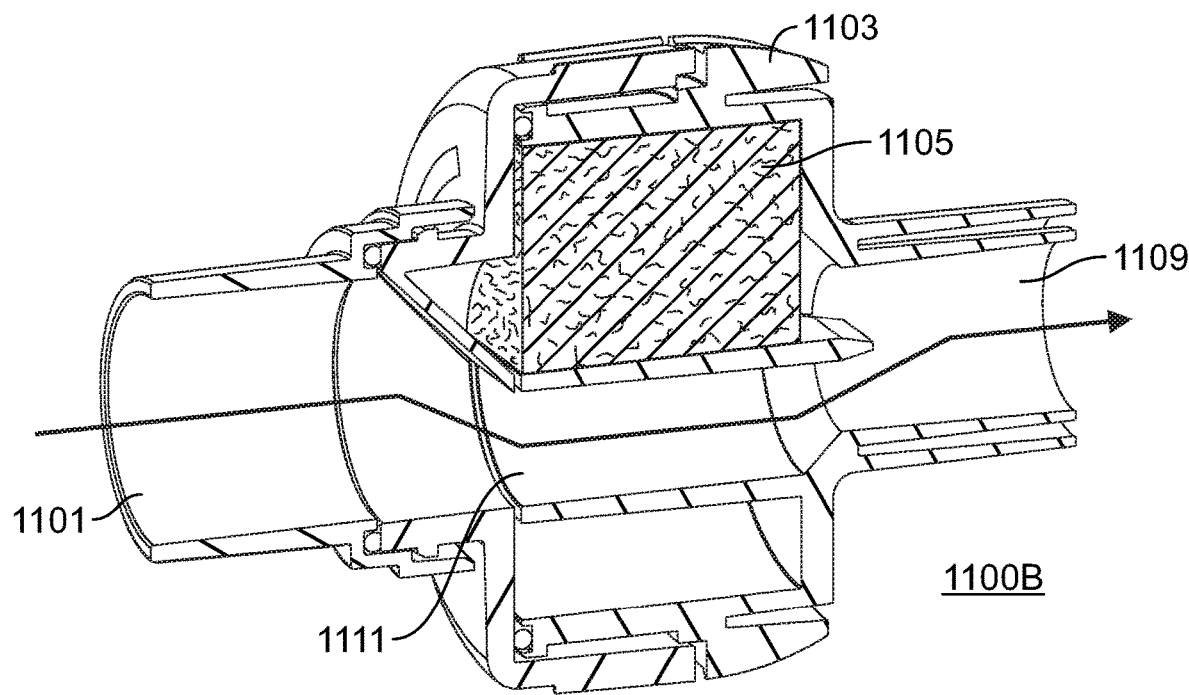
FIG. 11B is a cross-sectional view of the HME shown in FIG. 8B illustrating an closed bypass.
Figure 11A:
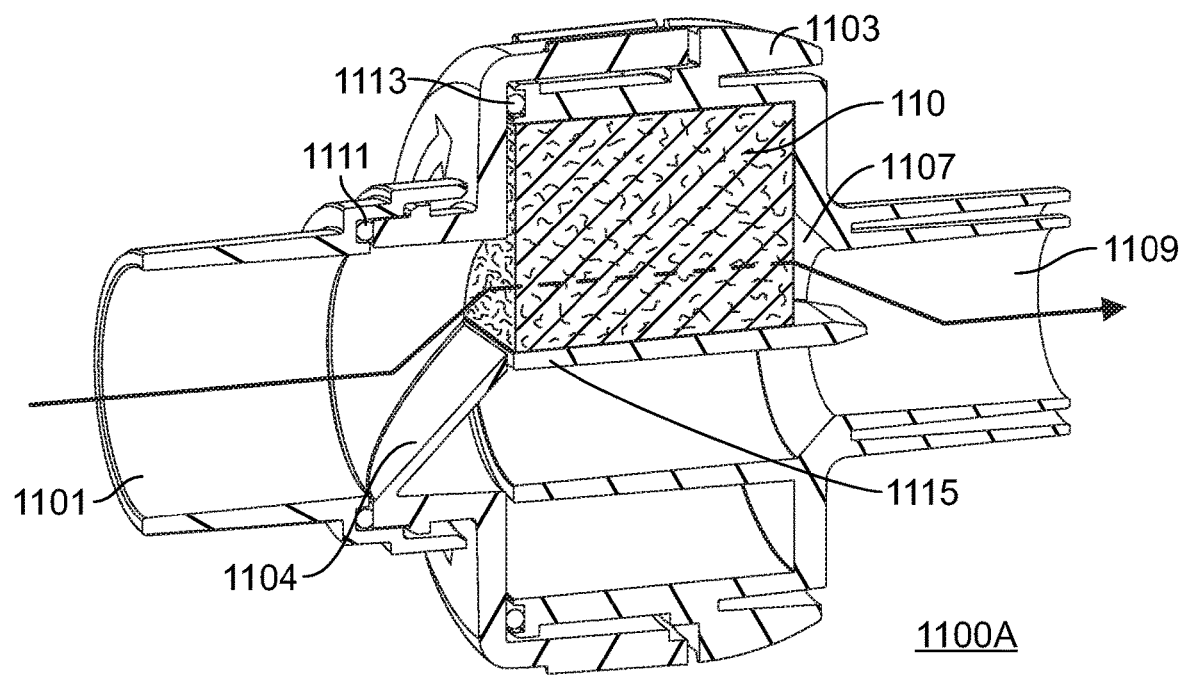
FIG. 11A is a cross-sectional view of the HME shown in FIG. 8A illustrating an open bypass.

FIG. 11A is a cross-sectional view of the HME shown in FIG. 8A illustrating an HME off or bypass mode where air is passed though the foam insert. More specifically, when the HME is rotated to an operational or aerosol on ("AERO ON") position, so the HME 1100A operates by directing air at the input port 1101 though the rotating cylinder 1103 formed by the first housing and second housing. The air contacts a diverter 1104 where it is directed into the foam insert 1105. The diverter is an angled or ramped member that operates by diverting, deflecting and/or changing the direction of airstream towards the foam insert 1105. The diverter 1104 extends between a side of the input port 1101 to a support member 1115 extending below a foam insert 1105.

Thus, in use, the airstream passes though the foam insert 1105 where the air can be heated and humidified. It is then directed though an exit aperture 1107 where the airstream is guided though the exit port 1109. The foam insert 1105 is in the shape of a half-cylinder which reduce air flow resistance and lends itself well to easy and inexpensive replacement. Those skilled in the art will recognize that the configuration as defined herein allows for low air resistance and unrestricted airflow permitting the clinician to fully utilize any type of aerosolized medication. The O-ring 1111 provides a tight seal between the rotating input port 1101 while O-ring 1113 provides a tight seal between the first housing and second housing.

FIG. 11B is a cross-sectional view of the HME shown in a bypass mode where the first and second housing forming the rotating cylinder are rotated 90 degrees to that shown in FIG. 11A. In this configuration, HME 1100B is shown where air enters the input port 1101 and passes directly around the foam insert 1105. This configuration directs the airstream though the bypass channel 1111 where it is isolated from the foam insert 1105. After passing the foam insert 1105, the air exits though exit port 1109. As seen with regard to FIG. 11A and FIG. 11B, the rotating cylinder is configured to create a rotational bypass to air moving between the first port and second port such that the rotating cylinder can be moved between a position for engaging the foam insert.

Thus, the bypass heat and moisture exchanger (HME) is designed to provided humidification to patients being mechanically ventilated through and artificial airway. It is place in the ventilator circuit between the "wye" and the patient's artificial airway. The HME has two modes of operation viz. an "HME" 'mode where humidification to be delivered to the patient and "aero" mode that allows aerosolized medication to be delivered to the patient. The HME mode is engaged by rotating the HME's cylindrical housing so the foam insert is in the path of ventilation. The HME utilizes a treated foam to collect water vapor exhaled from the patient. The water vapor captured in the foam insert is warm because it was exhaled from the patient's body. During the inhalation portion of the breathing cycle, the inhaled breath will be humidified and warmed from the water vapor that has collected in the treated foam. The aero mode is made by rotating the HME material such as a foam insert out of the path ventilation. The HME can remain in the ventilator circuit for up to 72 hours.

Thus an embodiment of the invention includes a heat moisture exchanger (HME) having a rotatable bypass channel that includes a rotating cylinder having a first port and an outer cylinder having a second port attached to the rotating cylinder. A foam insert is configured within the rotating cylinder to provide humidity and moisture to the air moving though the HME using the patient inhalation and exhalation breaths. The rotating cylinder is configured to create a rotational bypass to air moving between the first port and second port such that the rotating cylinder can be moved between a position for engaging or bypassing the foam insert.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A heat moisture exchanger (HME) comprising:
   a first housing having a first port;
   a second housing having a second port attached to a first housing cylinder;
   at least one foam insert configured within the first housing;
   at least one O-ring for preventing air from escaping from the first housing;
   an angled diverter of the second housing;
   wherein the first housing and second housing form a rotating cylinder that is configured to create a rotational bypass channel between the first port and second port, wherein the angled diverter is configured to direct air through the rotational bypass channel in a bypass mode, and the angled diverter is configured to direct air through the at least one foam insert in an HME mode;
   a support member of the first housing, the support member comprising a first flat surface, a second flat surface opposite to the first flat surface and a third flat surface extending from the first flat surface to the second flat surface;
   a bypass chamber at least partially defined by the first flat surface of the support member, wherein the bypass chamber forms part of the rotational bypass channel;
   an HME chamber at least partially defined by the second flat surface of the support member, wherein the at least one foam insert is positioned in the HME chamber, and the at least one foam insert is in a shape of a half-cylinder;
   wherein the angled diverter forming a planar plate comprising a first flat surface that is angled relative to a longitudinal axis of the HME, the first flat surface of the angled diverter configured to direct air through the rotational bypass channel in the bypass mode, and the first flat surface of the angled diverter is configured to direct air through the at least one foam insert in the HME mode;

wherein the angled diverter further comprises a second surface opposite to the first flat surface of the angled diverter and a third surface that extends from the first flat surface of the angled diverter to the second surface of the angled diverter, the second surface of the angled diverter is configured to face the at least one foam insert in the bypass mode and does not face the bypass chamber in the bypass mode and the second surface of the angled diverter is configured to face the bypass chamber in the HME mode and does not face the at least one foam insert in the HME mode; and wherein the third surface of the angled diverter is configured to directly face the third flat surface of the support member in the bypass mode and configured to directly face the third flat surface of the support member in the HME mode.

2. The HME of claim 1, wherein the first port is a rotating mask port.

3. The HME of claim 1, wherein a volume of the HME chamber is larger than a volume of the bypass chamber.

4. The HME of claim 1, wherein a distal end of the angled diverter is a linear edge.

5. The HME of claim 4, wherein the linear edge is aligned with the support member in the bypass mode in a first rotational orientation, and wherein the linear edge is aligned with the support member in the HME mode in a second rotational orientation that is offset from the first rotational orientation by 180 degrees.

6. A heat moisture exchanger (HME) for use with medical ventilation equipment, the HME comprising:
a first housing having an aerosol chamber and a bypass chamber, wherein the aerosol chamber is configured to receive air through at least one foam insert for providing humidified air when in an engaged position and configured to receive air through the bypass chamber when in a bypass position, allowing air to bypass the at least one foam insert;
a second housing enclosing an end of the first housing and configured to indicate an operational position of the HME;
at least one O-ring for sealing air within the first housing;
wherein the first housing and second housing form a rotating cylinder that is configured to create a rotational bypass channel between a first port of the first housing and a second port of the second housing, wherein the rotational bypass channel includes the bypass chamber of the first housing, and wherein an angled diverter of the second housing is configured to direct air through the rotational bypass channel in the bypass position, and the angled diverter is configured to direct air through the aerosol chamber and the at least one foam insert in the engaged position;
a support member of the first housing, the support member comprising a first flat surface, a second flat surface opposite to the first flat surface and a third flat surface extending from the first flat surface to the second flat surface, wherein the bypass chamber is at least partially defined by the first flat surface of the support member, and the aerosol chamber is at least partially defined by the second flat surface of the support member, wherein the at least one foam insert is positioned in the aerosol chamber, and the at least one foam insert is in a shape of a half-cylinder;
wherein the angled diverter forming a planar plate comprising a first flat surface that is angled relative to a longitudinal axis of the HME, the first flat surface of the angled diverter configured to direct air through the rotational bypass channel in the bypass position, and the first flat surface of the angled diverter is configured to direct air through the at least one foam insert in the engaged position;
wherein the angled diverter further comprises a second surface opposite to the first flat surface of the angled diverter and a third surface that extends from the first flat surface of the angled diverter to the second surface of the angled diverter, the second surface of the angled diverter is configured to face the at least one foam insert in the bypass position and does not face the bypass chamber in the bypass position and the second surface of the angled diverter is configured to face the bypass chamber in the engaged position and does not face the at least one foam insert in the engaged position; and
wherein the third surface of the angled diverter is configured to directly face the third flat surface of the support member in the bypass position and configured to directly face the third flat surface of the support member in the engaged position.

7. The HME of claim 6, further comprising a mask port connected to the first housing for connecting to a patient breathing mask, wherein the mask port is positioned proximate to the first port.

8. The HME of claim 7, where the mask port is rotatable.

9. The HME of claim 6, further comprising an input port connected to the second housing for connection to medical ventilation equipment, wherein the input port is positioned proximate to the second port.

10. The HME of claim 6, wherein the first housing includes a key on an outer surface of the first housing, and the second housing includes a keyway in an outer surface of the second housing for limiting rotational movement of the second housing.

11. A method of configuring a heat moisture exchanger HME) for use with medical ventilation equipment comprising:
configuring a first housing having an HME chamber and a bypass chamber where the HME chamber houses at least one foam insert for providing humidified air when in an engaged position, wherein the at least one foam insert is in a shape of a half-cylinder;
configuring a second housing such that the second housing encloses an end of the first housing and providing an indication of an operational position of the HME based on a position of the first housing;
rotating the first housing between the engaged position where air is directed into the at least one foam insert and a bypass position so that a patient's inhalation and exhalation breath is directed through the HME into either the HME chamber or the bypass chamber;
forming a rotating cylinder using the first housing and second housing that are sealed using a plurality of O-rings, wherein the rotating cylinder has a rotational bypass channel between a first port of the first housing and a second port of the second housing, wherein the rotational bypass channel includes the bypass chamber of the first housing, and wherein an angled diverter of the second housing is configured to direct air through the rotational bypass channel in the bypass position, and the angled diverter is configured to direct air through the HME chamber and the at least one foam insert in the engaged position;

forming a support member of the first housing, the support member comprising a first flat surface, a second flat surface opposite to the first flat surface and a third flat surface extending from the first flat surface to the second flat surface, wherein the bypass chamber is at least partially defined by the first flat surface of the support member, and the HME chamber is at least partially defined by the second flat surface of the support member; and forming a planar plate of the angled diverter, the planar plate comprising a first flat surface that is angled relative to a longitudinal axis of the HME, the first flat surface of the angled diverter configured to direct air through the rotational bypass channel in the bypass position, and the first flat surface of the angled diverter is configured to direct air through the at least one foam insert in the engaged position, the angled diverter further comprises a second surface opposite to the first flat surface of the angled diverter and a third surface that extends from the first flat surface of the angled diverter to the second surface of the angled diverter, the second surface of the angled diverter is configured to face the at least one foam insert in the bypass position and does not face the bypass chamber in the bypass position and the second surface of the angled diverter is configured to face the bypass chamber in the engaged position and does not face the at least one foam insert in the engaged position, and wherein the third surface of the angled diverter is configured to directly face the third flat surface of the support member in the bypass position and configured to directly face the third flat surface of the support member in the engaged position.

12. The method of configuring the HME of claim 11, further comprising:

forming a rotatable mask port with the first housing for connecting to a patient breathing mask, wherein the rotatable mask port is positioned proximate to the first port; and forming an input port with the second housing for connection to ventilation equipment, wherein the input port is positioned proximate to the second port.

13. The method of configuring the HME of claim 11, further comprising:

providing a key on an outer surface of the first housing and a keyway on an outer surface of the second housing for limiting rotational movement of the second housing between an engaged mode and bypass mode.

* * * * *